United States Patent [19]
de Toledo

[11] Patent Number: 4,932,419
[45] Date of Patent: Jun. 12, 1990

[54] MULTI-FILAR, CROSS-WOUND COIL FOR MEDICAL DEVICES

[75] Inventor: Fernando A. de Toledo, Concord, Mass.

[73] Assignee: Boston Scientific Corporation, Watertown, Mass.

[21] Appl. No.: 170,514

[22] Filed: Mar. 21, 1988

[51] Int. Cl.$^5$ .......................................... A61M 25/00
[52] U.S. Cl. ...................................... 128/772; 128/657
[58] Field of Search ................. 604/95, 170; 128/341, 128/343, 344, 656–658, 772

[56] References Cited

U.S. PATENT DOCUMENTS

| | | | |
|---|---|---|---|
| 623,022 | 4/1899 | Johnson | 604/264 |
| 707,775 | 8/1902 | Harris | 604/264 |
| 2,118,631 | 5/1938 | Wappler | 128/349 |
| 2,560,915 | 7/1951 | Bamberger | 128/350 |
| 3,467,101 | 9/1969 | Fogarty et al. | 128/348 |
| 3,552,384 | 1/1971 | Pierie et al. | 128/657 |
| 3,749,085 | 7/1973 | Willson et al. | 128/2 B |
| 3,749,086 | 7/1973 | Kline et al. | 128/2 M |
| 3,757,768 | 9/1973 | Kline | 128/772 |
| 3,773,034 | 11/1973 | Burns et al. | 128/2 M |
| 3,841,308 | 10/1974 | Tate | 128/772 |
| 4,020,829 | 5/1977 | Willson | 128/772 |
| 4,052,989 | 10/1977 | Kline | 128/349 R |
| 4,068,660 | 1/1978 | Beck | 128/214.4 |
| 4,173,981 | 11/1979 | Mortensen | 128/348 |
| 4,222,380 | 9/1980 | Terayama | 128/216 |
| 4,307,722 | 12/1981 | Evans | 128/344 |
| 4,318,402 | 3/1982 | Vaillancourt | 128/214.4 |
| 4,351,341 | 9/1982 | Goldberg et al. | 128/348 |
| 4,368,730 | 1/1983 | Sharrock | 604/158 |
| 4,444,188 | 4/1984 | Bazell et al. | 128/348.1 |
| 4,493,696 | 1/1985 | Uldall | 604/43 |
| 4,548,206 | 10/1985 | Osborne | 128/772 |
| 4,561,439 | 12/1985 | Bishop et al. | 128/348.1 |
| 4,642,092 | 2/1987 | Moss | 604/43 |
| 4,676,249 | 6/1987 | Arenas et al. | 128/657 |
| 4,692,153 | 8/1987 | Berlin et al. | 604/171 |
| 4,715,378 | 12/1987 | Pope, Jr. et al. | 128/344 |
| 4,719,924 | 1/1988 | Crittenden et al. | 128/657 X |
| 4,779,628 | 10/1988 | Machek | 128/772 |

OTHER PUBLICATIONS

U.S.C.I. Literature.

Primary Examiner—Dalton L. Truluck

[57] ABSTRACT

A flexible catheter-like guidewire has a multi-filar, cross-wound coil body terminating in a distal ball tip element. The body has a first inner coil of multiple coil wires wound in a first helical direction and a second outer coil of multiple coil wires disposed thereabout and wound in a second opposite helical direction. The body defines an elongated lumen opening proximally. The guidewire further includes a proximal handle and, extending therefrom, a core sized and adapted to be received through the proximal opening into the body lumen. The core, by movement of the handle relative to the body, is adapted for axial movement within the body for adjustment of the flexibility of the distal region of the device. A proximal connector joins the lumen, with the core removed, to a source of fluid, and a sheath associated with the body seals the lumen for transport of fluid introduced through the proximal opening, through the lumen to be delivered radially from the lumen in the distal tip region of the device.

24 Claims, 1 Drawing Sheet

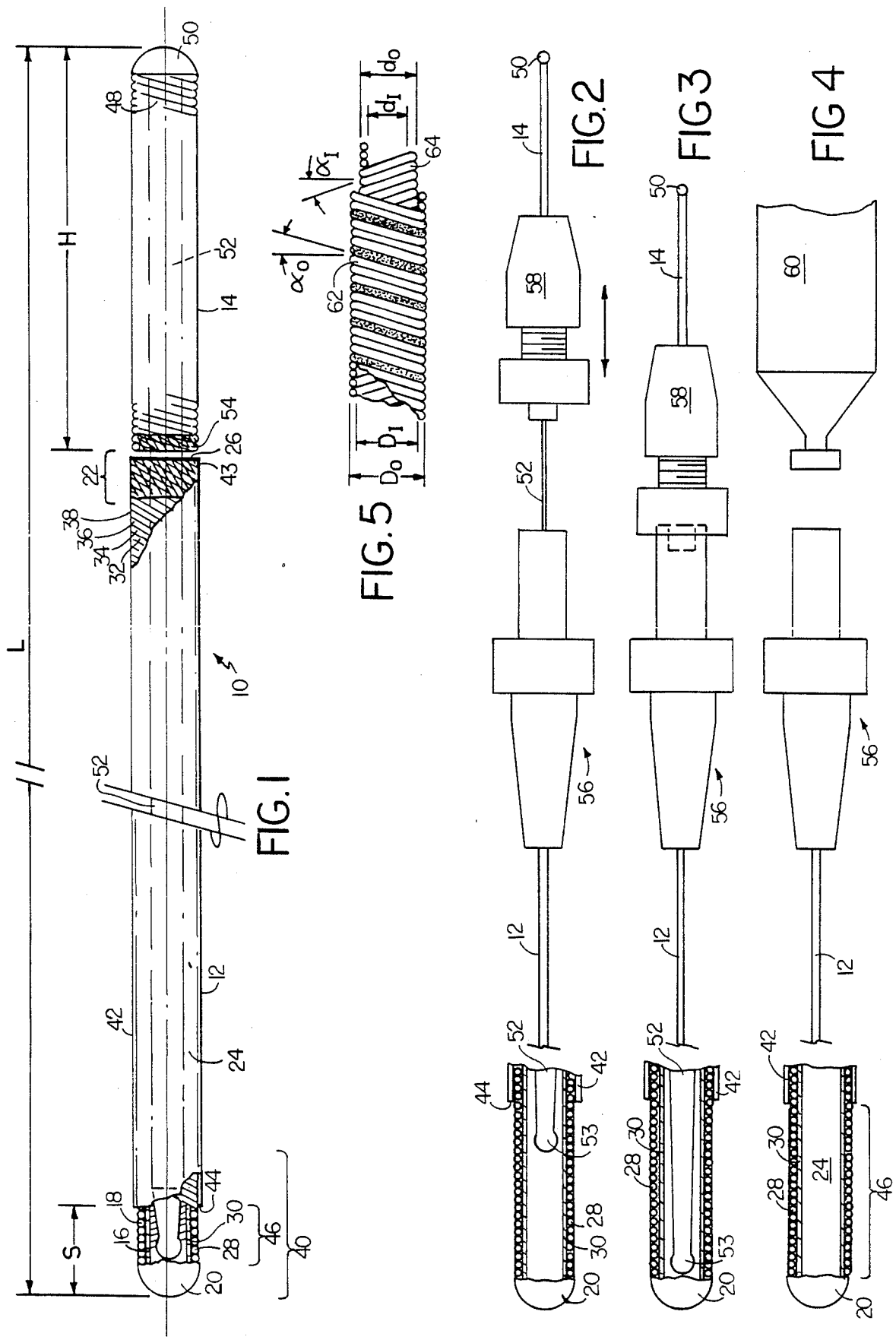

MULTI-FILAR, CROSS-WOUND COIL FOR MEDICAL DEVICES

BACKGROUND OF THE INVENTION

The invention relates to medical devices formed of multi-filar, cross-wound coils, and in particular to catheter-like devices so formed.

Medical devices consisting of elongated spring coils are employed widely as guidewires, e.g., for negotiating tortuous and narrow passageways of the body to a site to be treated and then serving as guides for catheters or other larger diameter devices advanced over the guidewires. In order to obtain maximum performance and patient safety, it is important that the guidewire be as small in diameter as possible, particularly in the tip region (but not so small as to create a danger of the tip breaking loose in the body); that the distal tip region be highly flexible to permit negotiation of difficult turns within the body; that the guidewire also be stiff enough axially to be advanced by pressure from the proximal end outside the body; and that the guidewire have good steerability or torque response, i.e., the tip to handle turn ratio should be as close to 1:1 as possible, without whipping. Most prior art guidewires offer or comprise of these desired features, e.g., trading tip flexibility for good torque response Another use of spring coils is in catheter-like medical devices which require characteristics similar to those described above. An example of such a device is described in Tate U.S. Pat. No. 3,841,308 as having a spring coil covered with a polyfluoroethylene flexible coating or sheath for delivery of fluid to ports adjacent the distal end.

SUMMARY OF THE INVENTION

According to the invention, a flexible catheter-like guidewire device comprises a multi-filar, cross-wound coil body terminating in a distal ball tip element, the body comprising a first inner coil of multiple coil wires wound in a first helical direction and a second outer coil of multiple coil wires disposed thereabout and wound in a second opposite helical direction, the body defining an elongated lumen opening proximally, a proximal handle portion and, extending therefrom, a core sized and adapted to be received through the proximal opening into the lumen of the body, the core, by movement of the handle relative to the body, adapted for axial movement within the body for adjustment of the flexibility of the distal region of the device, proximal means for connection of the lumen, with the core removed, to a source of fluid, and sheath means associated with the body for sealing the lumen for transport of fluid introduced through the proximal opening, through the lumen, to be delivered radially from the lumen in the distal tip region of the device Preferred embodiments of this and other aspects of the invention may include one or more of the following features. The wire of the inner coil is a flat wire, preferably wound in a bifilar coil and at a pitch of about 2:1. The wire of the outer coil is a round wire, preferably wound in a quadrifilar coil, and at a pitch of about 4:1. The sheath means comprises a Teflon ® shrink tube extending generally from adjacent the proximal opening of the lumen to a region spaced proximally from the distal end of the device, preferably the tube is disposed about the outer coil or between inner and outer coils. The proximal means for connection comprises a Touhy-Borst female connector. The device further comprises a Touhy-Borst male connector attached to the handle and adapted to engage with the female connector for locking the core fully disposed within the lumen. The inner coil is connected to the outer coil in a distal region and in a proximal region, preferably the inner coil and outer coil are connected at least at the distal ball tip element, and adjacent the proximal opening to the lumen. The body is adapted for transmission, to the distal tip region, of substantially all of the rotation torque applied to the proximal end of the device outside of the body.

According to another aspect of the invention, an elongated, medical guidewire device comprises a multi-filar, cross-wound coil body terminating in a distal ball tip element, the body comprising a first inner coil of multiple coil wires wound in a first helical direction and a second outer coil of multiple coil wires disposed thereabout and wound in a second opposite helical direction, the body defining an elongated open lumen, the inner coil being connected to the outer coil in a distal region and in a proximal region, the body being adapted for transmission, to the distal tip region, of substantially all of the rotation torque applied to the proximal end of the device outside of the body.

Thus there is provided an elongated spring coil medical device of improved design, consisting of multi-filar, cross-wound coils and resulting in improved torque response and steerability, tip design freedom, high axial pull strength and improved patient safety, and an open-ended lumen for adaptability of design.

In the preferred embodiment now to be described, the open lumen alternately receives a movable core for adjustment of tip flexibility and provides means for delivery of fluid through the device to a treatment site.

These and other features and advantages of the invention will be seen from the following description of a presently preferred embodiment, and from the claims.

PREFERRED EMBODIMENT

We first briefly describe the drawings.

FIG. 1 is a side view, partially in section, of a multi-filar, cross-wound spring coil medical device of the invention, in this case in the form of an injection guidewire;

FIG. 2 is a somewhat diagrammatic view of the device of FIG. 1 showing the movable core withdrawn relative to the coil body for adjustment of distal tip region flexibility;

FIG. 3 is a similar view of the device of FIGS. 1 and 2 with male and female Touhy-Borst components engaged to lock the movable core in the forward/stiff position;

FIG. 4 is a view similar to that of FIGS. 2 and 3 of the device with the movable core removed to provide an open lumen for introduction of fluid to a treatment site; and FIG. 5 is a side view partially in section of an alternate embodiment of the multi-filar, cross-wound coil body of the invention, formed of two round wire coils.

The multi-filar, cross-wound coil device of the invention, i.e., injection catheter 10, of length L, e.g., 145 cms, and of nominal outer diameter 0.035/0.038 inch, consists of a body portion 12 and a handle portion 14. The body portion 12 is formed of a first, inner coil 16 and a second, outer coil 18 joined distally at a ball tip element 20 and joined proximally, e.g., by soldering, at region 22. The body thus defines an open inner lumen 24 terminating proximally at opening 26.

The first, inner coil 16 is bifilar, formed of two flat wires 28, 30, e.g., 0.003 inch by 0.010 inch, closely wound at a pitch ratio of about 2:1. The outer coil is quadrifilar, formed of four circular cross-section wires 32, 34, 36, 38, of 0.025 inch diameter wire, which are similarly closely wound thereabout, but in a direction opposite to the winding direction of the first, inner coil and with a ratio of 4:1. The resulting assembly provides a coil body portion of high axial pull strength, e.g., permitting safe use of a medical device without a core fixed to the distal tip or a safety wire. This allows greater tip design freedom. It also results in a device having good torque response and steerability, with the distal tip region 40 responding at almost a 1:1 ratio to rotational force applied to the proximal end of the device.

A sheath 42 of liquid impermeable heat shrink material, e.g., Teflon® or the like, is disposed about the body portion, from the proximal end 43, adjacent the proximal opening 26, to terminate at 44 at a distance, S, from the distal tip, e.g., 12 mm, adjacent, but spaced from the distal tip element 20, leaving a segment 46 of the outer coil exposed.

Handle portion 14, of length H, e.g., 5 cm, single round wire coil 48, terminating proximally in a ball weld element 50, disposed about an elongated core wire 52. The core wire is joined to the coil at the proximal element 50 and also at the distal end of the handle element, e.g., by soldering at 54. The core is sized to extend through the open lumen 24 of the body portion 12 and to be movable therewithin, as described more fully below.

Affixed at the proximal end of the body portion 12 of the device, adjacent the proximal opening, is a connector, in this case a Touhy-Borst (female) connector 56. Affixed at the distal end of the handle portion 14 is a complementary Touhy-Borst (male) connector 58.

Referring to FIG. 2, the handle portion 14 is movable relative to the body portion 12, to adjust the position of the movable core 52 within the body lumen 24, and thereby adjust the flexibility of the tip region 40 of the device within the patient's body to facilitate negotiation of difficult passageways. In FIG. 2, the distal tip 53 of the core 52 is spaced from the distal ball element 20, for maximum flexibility of the distal region. (The multifilar, cross-wound construction of the invention provides the advantage of high axial pull strength, permitting the device to be made without a safety wire, or core attached to the distal ball element.) Referring to FIG. 3, the movable core 52 is shown in the forward/stiff position, and the body and handle portions are locked together by interengagement of Touhy-Borst connector components 56, 58. In either relationship, the body portion of the device may be steered accurately, with good torque response, by rotation of the proximal region of the body at 22 transmitted to the distal tip region 40 with substantially a 1:1 ratio due to the characteristics of the multi-filar, cross-wound coils of the device body portion. (Typically, the physician operating the device will provide a hook or bend in the distal region 40 so rotation of the device will allow the tip to enter or negotiate side passageways or turns.)

Referring to FIG. 4, for treatment of a site within the body, the distal tip region 40 is advanced to a desired location within the patient's body. The movable core 54 is removed and a syringe 60 (or other source of fluid) is attached to the Tuohy-Borst female connector 56. Fluid introduced via opening 26 into the lumen 24 flows within the lumen, contained by fluid impermeable sleeve, to region 46, to seep between the coils of inner and outer coils, distal of the sleeve, into the patient, e.g., for treatment of a disorder.

Referring to FIG. 5, in which an alternate embodiment of the device is shown, consisting of cross-wound multi-filar coils of circular cross-section wires, the coils 62, 64 are each manufactured by winding four round cross-section wires of size about 0.004 inch diameter, so that $D_0$ is about 0.032 inch, $D_1$ is about 0.024 inch, $d_0$ is about 0.024 inch and $d_1$ is about 0.016 inch. The coils are closely wound with a pitch angle $\alpha_0$ and $\alpha_1$ where $\alpha_0$ is smaller than $\alpha_1$ e.g., 15° and 15°, respectively. (Flat wires having a cross-sectional depth of about 0.1 mm may also be used.) The pitch angles are chosen to eliminate clearances between the wires and to apply a substantial part of the stress in either tension or compression along the axis of the wire filaments.

To form inner coil 64, four individual round wires (or two flat wires in the embodiments of FIGS. 1-4) are simultaneously wound around a mandrel of about 0.016 inch outer diameter. The free ends of this coil are fixed, and then, to form the second coil 62 thereabout, four wires are wound in opposite hand directly over coil 64. The wires are wound under moderate tension, of about 22.5 gm/wire. After winding, the coils are released. The inner mandrel, which may have a constant cross-sectional diameter, or may be tapered or stepped, is then removed. The wire ends are finished by grinding. The proximal ends are then soldered to fix the coils together for a distance of about 3 mm. This end is held in a rigid support and the coils are then twisted sufficiently, e.g., ¼ turn, to cause the outer coil to compress and the inner coil to expand, causing the coils to interfere. The free ends are then also fixed. The coil assembly is generally formed from wires which provide a low spring index, that is, the radius of the outer coil must be not more than about 2.5 to 10 times the diameter of the wires used in its construction. With a higher index, the inner coil may collapse. The multifilar nature of the coils enables a smaller diameter coil to be employed, which is of particular importance for vascular catheters and other spring coil medical devices where small size is important.

Other embodiments are within the following claims. For example, the sleeve may be disposed between the inner and outer coils. Also, one or more of the coil wires, at least in the distal region, may be of material of relatively high radiopacity, e.g., platinum or the like. If desired, the quadrifilar coil may instead be bifilar or trifilar, or made up of more strands than four.

I claim:

1. A flexible catheter-like guidewire device comprising a multi-filar, cross-wound coil body terminating in a distal ball tip element, said body comprising a first inner coil of multiple coil wires wound in a first helical direction and a second outer coil of multiple coil wires disposed closely thereabout and wound in a second opposite helical direction, said body defining an elongated lumen opening proximally, said distal ball tip element attached to said body solely via said inner and outer coil wires, a proximal handle portion, a core extending from said handle portion and removably received through the proximal opening into the elongated lumen of said body, said core, by movement of said handle relative to said body, adapted for axial movement within said body, relative to said distal ball tip element, for adjustment of the axial position of said core relative to said body thereby to vary the flexibility of the distal region of the device, proximal means connected to said coil body for connection of said lumen, with said core removed, to a source of fluid, and sheath means secured about said body for sealing said lumen for transport of fluid introduced through the proximal opening, through said lumen, to be delivered radially from said lumen in the distal tip region of the device.

2. The catheter-like guidewire device of claim 1 wherein the wire of said inner coil is a flat wire.

3. The catheter-like guidewire device of claim 2 wherein said flat wire of said inner coil is wound in a bifilar coil.

4. The catheter-like guidewire device of claim 3 wherein said bifilar coil is wound at a pitch of about 2:1.

5. The catheter-like guidewire device of claim 1 wherein the wire of said outer coil is a round wire.

6. The catheter-like guidewire device of claim 5 wherein said round wire is wound in a quadrifilar coil.

7. The catheter-like guidewire device of claim 6 wherein said quadrifilar coil is wound at a pitch of about 4:1.

8. The catheter-like guidewire device of claim 1 wherein said sheath means comprises a Teflon ® shrink tube extending generally from adjacent the proximal opening of said lumen to a region spaced proximally from the distal end of said device.

9. The catheter-like guidewire device of claim 8 wherein said tube is disposed about said outer coil.

10. The catheter-like guidewire device of claim 8 wherein said tube is disposed between said inner and outer coils.

11. The catheter-like guidewire device of claim 1 wherein said proximal means for connection comprises a Touhy-Borst female connector.

12. The catheter-like guidewire device of claim 11 wherein said device further comprises a Touhy-Borst male connector attached to said handle and adapted to engage with said female connector for locking said core fully disposed within said lumen.

13. The catheter-like guidewire device of claim 1 wherein said inner coil is connected to said outer coil in a distal region and in a proximal region.

14. The catheter-like guidewire device of claim 13 wherein said inner coil and said outer coil are connected at least in said distal tip region.

15. The catheter-like guidewire device of claim 13 wherein said inner coil and said outer coil are connected at least adjacent said proximal opening to said lumen.

16. The catheter-like guidewire device of claim 1 wherein said body is adapted for transmission, to the distal tip region, of substantially all of the rotation torque applied to the proximal end of the device outside of the body.

17. An elongated, medical guidewire device comprising a multi-filar, cross-wound coil body terminating in a distal tip, said body comprising a first inner coil of multiple coil wires wound in a first helical direction and a second outer coil of multiple coil wires disposed closely thereabout in a manner to bear upon the inner coil during rotation of said device, and wound in a second opposite helical direction, said body defining an elongated open lumen, said inner coil being connected to said outer coil in a distal region and in a proximal region, said body comprising means for transmission, to the distal tip region, of substantially all of the rotation torque applied to the proximal end of the device outside of the body, said means comprising said second coil beds upon said first coil.

18. The guidewire device of claim 17 wherein the wire of at least one said coil is a flat wire.

19. The guidewire device of claim 18 wherein said flat wire is wound in a bifilar coil.

20. The guidewire device of claim 17 wherein the wire of at least one said coil is a round wire.

21. The guidewire device of claim 20 wherein said round wire is wound in a quadrifilar coil.

22. The guidewire device of claim 18 or 20 wherein said coil is wound at a pitch of about 4:1.

23. The guidewire device of claim 17 wherein said coils of said device define an open volume at least in said distal tip region.

24. The guidewire device of claim 1 or 17 wherein said multi-filar, cross wound coil body terminates distally in a distal ball tip element.

* * * * *

UNITED STATES PATENT AND TRADEMARK OFFICE
CERTIFICATE OF CORRECTION

PATENT NO.   :   4,932,419
DATED        :   June 12, 1990
INVENTOR(S)  :   Fernando A. deToledo It is certified that error appears in the above-identified patent and that said Letters Patent is hereby corrected as shown below:

Col. 1, line 27; insert --.-- at end of line;

Col. 1, line 56; insert --.-- at end of line;

Col. 3, line 7; change "0.025" to --0.005--;

Col. 4, line 33-36; delete "This end is ... to interfere."

Col. 4, line 42; change "multifilar" to --multi-filar--.

Signed and Sealed this

Thirty-first Day of December, 1991

*Attest:*

HARRY F. MANBECK, JR.

*Attesting Officer*     *Commissioner of Patents and Trademarks*